United States Patent
Chou et al.

(10) Patent No.: US 10,628,693 B2
(45) Date of Patent: Apr. 21, 2020

(54) DEVICES AND METHODS FOR AUTHENTICATING A SAMPLE AND USE OF THE SAME

(71) Applicant: Essenlix Corporation, Monmouth Junction, NJ (US)

(72) Inventors: Stephen Y. Chou, Princeton, NJ (US); Wei Ding, East Windsor, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

(21) Appl. No.: 16/329,815

(22) PCT Filed: Dec. 21, 2017

(86) PCT No.: PCT/US2017/068031
§ 371 (c)(1),
(2) Date: Mar. 1, 2019

(87) PCT Pub. No.: WO2018/119318
PCT Pub. Date: Jun. 28, 2018

(65) Prior Publication Data
US 2019/0220679 A1    Jul. 18, 2019

Related U.S. Application Data

(60) Provisional application No. 62/437,339, filed on Dec. 21, 2016.

(51) Int. Cl.
*G01N 1/00* (2006.01)
*G06K 9/00* (2006.01)
(Continued)

(52) U.S. Cl.
CPC ........ *G06K 9/00892* (2013.01); *A61B 5/0002* (2013.01); *A61B 5/0075* (2013.01); *A61B 5/0077* (2013.01); *A61B 5/082* (2013.01); *A61B 5/1032* (2013.01); *A61B 5/1079* (2013.01); *A61B 5/117* (2013.01); *A61B 5/1172* (2013.01); *A61B 5/1455* (2013.01);
(Continued)

(58) Field of Classification Search
CPC ....................................................... G01N 1/00
See application file for complete search history.

(56) References Cited

U.S. PATENT DOCUMENTS

| 3,368,872 A | 2/1968 | Natelson |
| 3,447,863 A | 6/1969 | Patterson |

(Continued)

FOREIGN PATENT DOCUMENTS

| AU | 198813789 A | 9/1988 |
| AU | 619459 B | 1/1992 |

(Continued)

OTHER PUBLICATIONS

Van Vliet, Dillys et al., Prediction of asthma exacerbations in children by innovative exhaled inflammatory markers: Results of a longitudinal study, PLOS ONE, Mar. 23, 2015, vol. 10. No. 3, e0119434.

(Continued)

*Primary Examiner* — Jyoti Nagpaul
(74) *Attorney, Agent, or Firm* — Essenlix Corporation

(57) ABSTRACT

Among other things, the present invention is related to devices and methods of authenticating test samples truly from a subject that will be tested, such as blood samples or exhaled breath condensation.

50 Claims, 3 Drawing Sheets

(51) Int. Cl.

| | |
|---|---|
| *A61B 5/00* | (2006.01) |
| *A61B 5/1172* | (2016.01) |
| *A61B 5/15* | (2006.01) |
| *G06K 9/46* | (2006.01) |
| *G16H 10/40* | (2018.01) |
| *G16H 50/20* | (2018.01) |
| *G16H 30/40* | (2018.01) |
| *A61B 5/08* | (2006.01) |
| *A61B 5/103* | (2006.01) |
| *A61B 5/107* | (2006.01) |
| *A61B 5/117* | (2016.01) |
| *A61B 5/145* | (2006.01) |
| *A61B 5/1455* | (2006.01) |
| *G06K 9/22* | (2006.01) |
| *A61B 10/00* | (2006.01) |

(52) U.S. Cl.
CPC ............ *A61B 5/14546* (2013.01); *A61B 5/15* (2013.01); *A61B 5/150022* (2013.01); *A61B 5/150343* (2013.01); *A61B 5/150358* (2013.01); *A61B 5/150763* (2013.01); *A61B 5/4277* (2013.01); *A61B 5/4848* (2013.01); *G06K 9/00087* (2013.01); *G06K 9/00093* (2013.01); *G06K 9/46* (2013.01); *G16H 10/40* (2018.01); *G16H 30/40* (2018.01); *G16H 50/20* (2018.01); *A61B 5/150305* (2013.01); *A61B 2010/0087* (2013.01); *A61B 2576/00* (2013.01); *A61B 2576/02* (2013.01); *G06K 9/00885* (2013.01); *G06K 9/22* (2013.01); *G06K 2009/00932* (2013.01); *G06K 2009/00946* (2013.01)

(56) References Cited

U.S. PATENT DOCUMENTS

| | | |
|---|---|---|
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |

(56) References Cited

U.S. PATENT DOCUMENTS

| | | |
|---|---|---|
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 2001/0055882 A1 | 12/2001 | Ostuni |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2009/0318834 A1 | 12/2009 | Fujiwara et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2014/0315242 A1 | 10/2014 | Rodriguez et al. |
| 2014/0368631 A1 | 12/2014 | Wardlaw et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0245797 A1 | 8/2016 | Ahmad et al. |
| 2016/0266091 A1 | 9/2016 | Levine et al. |
| 2017/0021356 A1 | 1/2017 | Dority et al. |
| 2017/0038401 A1 | 2/2017 | Holmes et al. |
| 2017/0045504 A1 | 2/2017 | Bloom |

FOREIGN PATENT DOCUMENTS

| | | |
|---|---|---|
| CN | 1299466 | 6/2001 |
| CN | 1302229 | 7/2001 |
| CN | 1166950 | 9/2004 |
| CN | 1188217 | 2/2005 |
| CN | 102027369 | 4/2011 |
| EP | 261667 A2 | 3/1988 |
| EP | 291153 A1 | 11/1988 |
| EP | 261667 A3 | 5/1989 |
| EP | 291153 B1 | 6/1992 |
| EP | 261667 B1 | 2/1993 |
| EP | 0961110 | 12/1999 |
| EP | 1949310 A2 | 7/2008 |
| EP | 2290100 | 3/2011 |
| EP | 1949310 A4 | 11/2011 |
| EP | 2439515 | 4/2012 |
| EP | 2554987 | 2/2013 |
| EP | 2848196 | 3/2015 |
| EP | 3026433 | 6/2016 |
| EP | 1949310 B1 | 2/2019 |
| WO | 1991020009 | 12/1991 |
| WO | 1999044743 | 9/1999 |
| WO | 1999045385 | 9/1999 |
| WO | 2003062920 | 7/2003 |
| WO | 2005114145 | 12/2005 |
| WO | 2005100539 | 1/2006 |
| WO | 2007112332 | 10/2007 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014055559 | 4/2014 |
| WO | 2014089468 | 6/2014 |
| WO | 2014183049 | 11/2014 |
| WO | 2014205576 | 12/2014 |
| WO | 2017048871 | 3/2017 |

OTHER PUBLICATIONS

Written Opinion for PCT/US2018/017713 established by ISA/KR, dated Jun. 20, 2018.

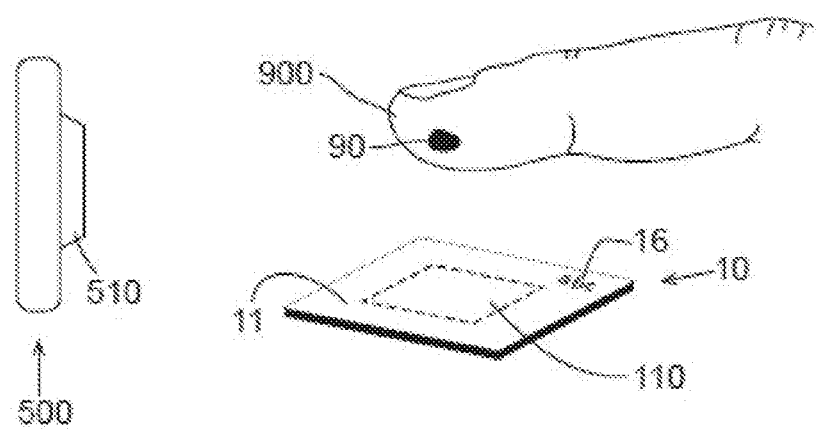
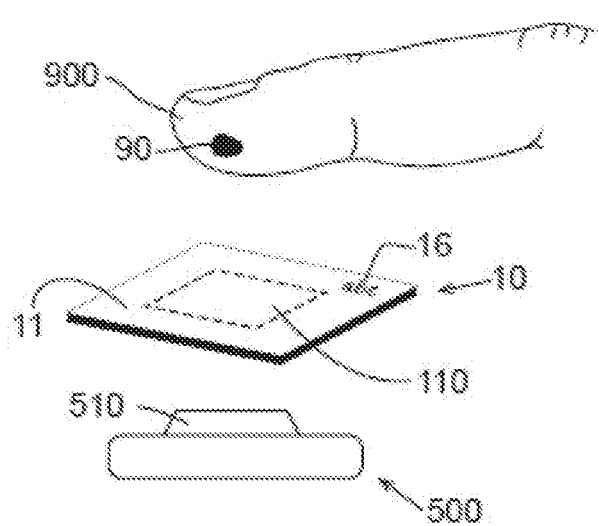
Fig. 1

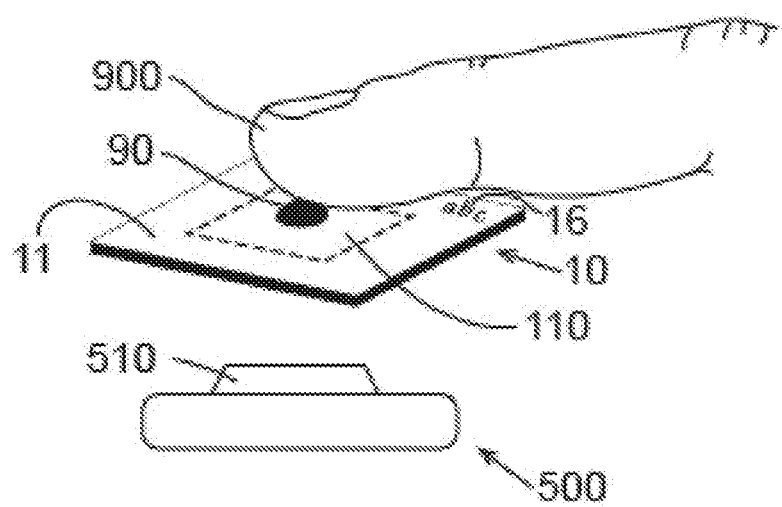
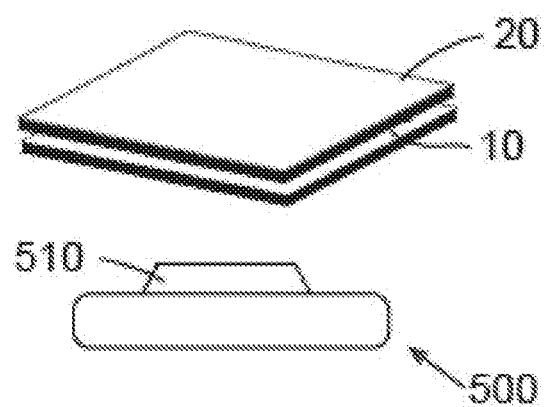
Fig. 2

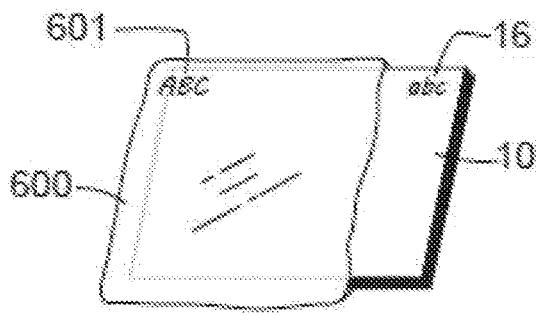
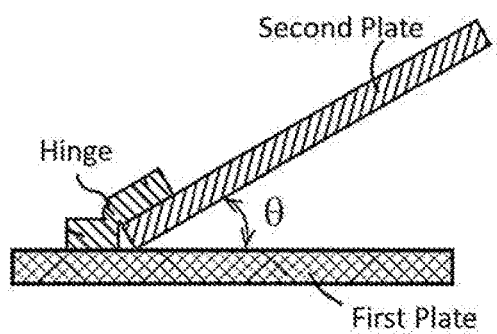
Fig. 3                    Fig. 4
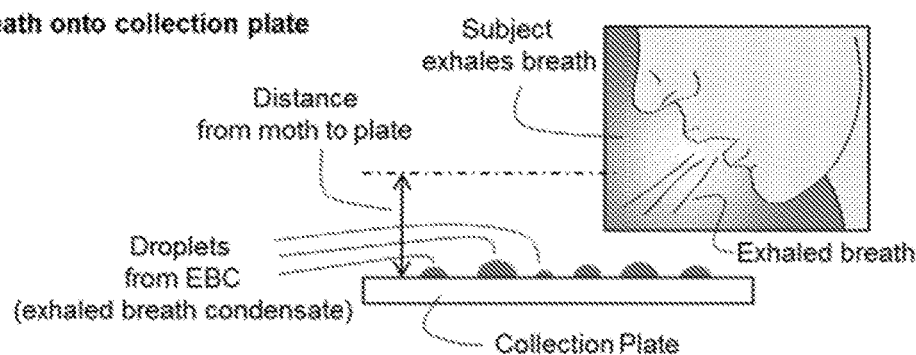
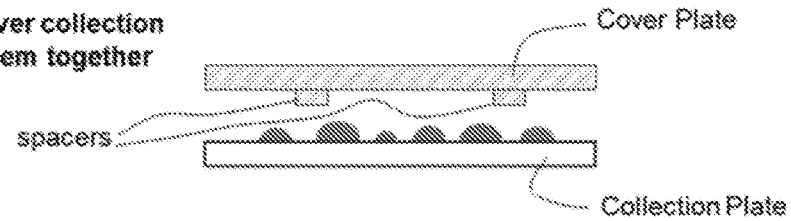
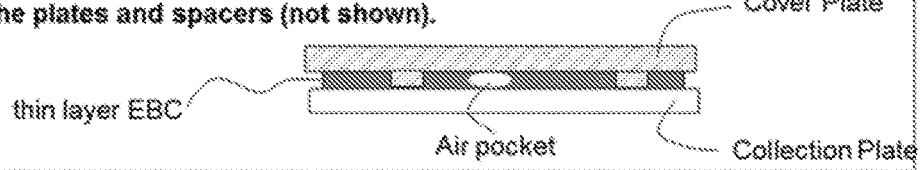
Fig. 5

DEVICES AND METHODS FOR AUTHENTICATING A SAMPLE AND USE OF THE SAME

CROSS-REFERENCING

This application is a PCT application and claims the benefit of U.S. Provisional Patent Application 62/437,339 filed on Dec. 21, 2016, which are incorporated herein in its entirety for all purposes.

FIELD

Among other things, the present invention is related to devices and methods of authenticating test samples truly from a subject that will be tested, such as blood samples or exhaled breath condensation.

BACKGROUND

In blood tests or exhaled breath condensation tests, it is important to authenticate the test because it is possible that someone other than the intended subject is actually tested, either inadvertently or deliberately. Here the term "intended subject" refers to a person that is scheduled/required to be tested in a specific blood-testing session by a testing professional, agency or entity. In some cases, for example, an imposter can replace the intended subject and provide a blood sample of his/her own; in some other circumstance, especially in remote blood testing, the intended subject can provide a blood sample not from himself/herself, but from someone else. Therefore, at least two problems arise: (1) authenticating that the subject being tested is actually the intended subject; and (2) authenticating that the sample being collected is actually a sample from the subject being tested, not from someone else. The present invention provides solutions to these problems.

BRIEF DESCRIPTION OF THE DRAWINGS

The skilled artisan will understand that the drawings, described below, are for illustration purposes only. The drawings are not intended to limit the scope of the present teachings in any way. In some Figures, the drawings are in scale. In the figures that present experimental data points, the lines that connect the data points are for guiding a viewing of the data only and have no other means.

FIG. 1 includes illustrations of exemplary embodiments of the present invention, showing different relative positioning of the camera and the test plate in panels (A) and (B).

FIG. 2 includes illustrations of exemplary embodiments of the present invention, showing the deposition of the blood sample in panel (A) and an embodiment including a cover plate in panel (B).

FIG. 3 includes an illustration of an exemplary embodiment of the present invention, showing a package for the test plate.

FIG. 4 includes an illustration of an exemplary embodiment of the present invention, showing a test plate that comprises a first plate and second plate that are movable to each other into different configurations.

FIG. 5 includes an illustration of an exemplary embodiment of the present invention, showing identification of a breath sample for a subject.

DETAILED DESCRIPTION OF EXEMPLARY EMBODIMENTS

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

In some blood tests, the subject that is being tested provides a drop of blood from a pricked body part, e.g. finger, arm or ear. Either directly or indirectly, the drop of blood is applied to a plate as a blood sample that would be tested. The present invention relates to devices and methods that authenticate a blood sample or an exhaled breath sample, and the present invention can be extended to authentication of other samples. In particular, with the devices and methods of the present invention, it can be determined: (1) whether the subject being tested is an intended subject; and (2) whether the blood sample deposited on the test plate is from the subject being tested, not from someone else.

One aspect of the present invention for sample authentication, e.g. a blood sample authentication or a breath sample authentication or One aspect of the present invention for the blood sample authentication is to use the blood sample from a pricked finger, deposit the blood sample directly from the pricked finger onto a test plate, and use a camera to record the deposition, wherein the recorded images comprises: (i) the blood sample on the pricked finger together with at least one biometric identifier associated with the hand to which the pricked finger belongs, and (ii) a video of a part or an entirety of the blood sample deposition process. For example, the biometric identifier can be: fingerprint of the pricked finger, fingerprint of a finger that is not pricked, palmprint of the hand, hand geometry of the hand, vein pattern of the hand, sweat pores of the hand, or fingernail beds of the hand.

The device and method of the present invention are used in health monitoring, mobile monitoring, and crime monitoring. In addition, the device and method the present invention can be used for insurance, for health improvement, for medication purposes.

Definition

The term "pricked finger" refers to a part of a hand of a subject, where the part is pricked by an instrument, so that the blood flows out from the subject to a surface of the part of the hand. The part of the hand can be any part of the hand, including but not limited to, fingers and palms.

The term "transparent plate" refers to a plate that a camera or an imager that is on one side of the plate to image an object on the other side of the plate.

The term "EBC" refers to exhaled breath condensation.

The term "a body part" refers to a part of body of a subject that can supply blood when pricked by an instrument. Example of a body part is finger, ear, and arm.

The term "sample contact area" and "sample receiving area" are interchangeable.

The term "intended subject" refers to a person that is scheduled/required to be tested in a specific blood-testing session by a testing professional, agency or entity.

The term "subject being tested" (or simply "subject") refers to a person that is participating in the blood-testing session; however, it is possible that the subject being tested is not the intended subject; and/or the subject being tested is not providing blood sample from his/her own pricked finger.

Blood Samples

In the description, the term "a pricked finger of a hand" is often used, however, the present invention is not limited to a pricked finger, but applies to other body parts of a subject as long as they can supply blood to outside of the body after pricked by an instrument.

In blood testing by pricking a body part of a subjection, a test plate is provided to the subject for a blood test, the subject goes through the process of providing a drop of blood for testing, a process that is also referred to as "blood sample deposition process." In some embodiments, the process includes:
  i. pricking a body part, such as a finger or an earlobe, of the subject; such pricking is conducted by the subject himself/herself or by someone else such as a medical professional;
  ii. producing a drop of blood from the pricked body part by squeezing; such squeezing is conducted by the subject himself/herself or by someone else such as a medical professional; in some embodiments, this step is omitted if the drop of blood can be produced without squeezing;
  iii. depositing all or part of the drop of blood from the pricked body part on the sample receiving surface; in some embodiments, the depositing is conducted by directly touching the sample receiving surface of the test plate with the pricked body part, e.g. pricked finger; In some embodiments, the drop of blood is deposited in the sample receiving area.

To authenticate the blood test, the identity of the subject being tested needs to be confirmed as the same for the intended subject. In some embodiments, the devices and methods of the present invention entails collecting at least one biometric identifier from the subject being tested. Here the term "biometric identifier" refers to biological traits related to human characteristics and such biological traits can be used to uniquely identify a human. The biometric identifier in the present invention includes but not is limited to: fingerprints, palmprints, hand geometry, vein patterns, sweat pores, fingernail beds, face, iris, retina, DNN, thermograms, gait, ear, skin tone, lip motion, body odor, and footprint.

As an example of the present invention, in blood test by pricked finger, a "biometric identifier" is the fingerprint that is surrounded to the blood drop which is coming off the finger that is pricked. With the devices and methods of the present invention, one can capture/record the blood of coming off the finger together with fingerprint.

In some embodiments, the devices and methods of the present invention use at least one biometric identifier related to the hand to which the pricked finger belongs to verify that the subject being tested is the intended subject; the biometric identifier related to the hand includes but is not limited to: fingerprint of the pricked finger, fingerprint of a finger that is not pricked, palmprint of the hand, hand geometry of the hand, vein pattern of the hand, sweat pores of the hand, and fingernail beds of the hand.

FIG. 1 shows the perspective views of two exemplary embodiments of the present invention. As shown in FIG. 1, panels (A) and (B), the device of the present invention comprises a test plate 10 and a camera 500. The test plate 10 comprises a sample receiving surface 11 that has a sample receiving area 110; the camera 500 comprises a lens 510. Also as shown in FIG. 1, panels (A) and (B), the test plate 10 is configured to receive a drop of blood 90 as a test sample from a pricked finger 900 of a subject that is being tested, and the drop of blood 90 is to be deposited on the sample receiving surface 11 by the subject. Herein the term "subject" refers to the individual who is using the test plate 10 for the blood test, and sometimes the term "subject being tested" is also used.

FIG. 2 shows the perspective views of two exemplary embodiments of the present invention. As shown in panel (A) of FIG. 2, and also referring to panel (B) of FIG. 1, the device of the present invention comprises a test plate 10 and a camera 500. The test plate 10 comprises a sample receiving surface 11 that has a sample receiving area 110; the camera 500 comprises a lens 510. Panel (B) of FIG. 4 shows an embodiment of the device, which comprises a camera 500, a test plate 10 and a cover plate 20.

As shown in FIGS. 3 and 4, in some embodiments, the sample receiving surface 11 comprises a sample receiving area 110. In some embodiments, the sample receiving area 110 occupies a part or the entirety of the sample receiving surface 11. In some embodiments, the sample receiving area 110 is clearly marked so that the subject easily deposits the drop of blood 90 into the sample receiving area 110. In certain embodiments, the test plate 10 comprises additional structures that are located in the sample receiving area 110, wherein such additional structures improve and/or facilitate the blood test. For example, the additional structures are spacers or grids.

To authenticate the blood test, a camera 500 is configured to capture videos and/or images of the subject, the hand, the finger 900, the drop of blood 90, and/or the test plate 10, as well as any features associated with these structures, such as but not limited to biometric identifiers (e.g. fingerprint of the finger 900) associated with the hand and certain characteristics (e.g. geometry, shape, size, position, color, light intensity, and/or light scattering) of the drop of blood 90. In certain embodiments, the video and/or image(s) are used to: (a) determine that the blood sample 90 from the prick finger 900 is actually deposited on the test plate; and (b) determine that the subject being tested is the intended subject.

In some embodiments, the camera 500 is configured to capture one or more images and/or one or more videos of the blood sample 90 before and/or after it is deposited on the test plate 10. Such image(s) and video(s) include at least one biometric identifier of the subject being tested; the biometric identifier is associated with the hand to which the pricked finger belongs. The descriptions below use fingerprint as an example; however, in some embodiments of the present invention, other biometric identifiers are captured, extracted and used for authentication purposes. The descriptions related to fingerprints also apply to other biometric identifiers.

In some embodiments, the camera 500 is configured to capture an image of the fingerprint of the pricked finger 900 during a process of providing the drop of blood 90 for testing. In certain embodiments, the camera 500 is configured to capture one or images of the fingerprints of the subject's fingers, including the pricked finger 900 and/or at least one un-pricked finger, during the process of providing the drop of blood 90 for testing. The image(s) of the fingerprint(s) are used to authenticate the blood test, for example, through a comparison of the fingerprint(s) to stored fingerprint information of the intended subject. In such a manner, it can be determined whether the subject using the test plate 10 is actually the intended subject. In some embodiments, the presence of the drop of blood 90 makes it more difficult for the camera 500 to capture an image of the entire fingerprint of the pricked finger 900.

Nevertheless, with known technology for partial fingerprint recognition (e.g. the devices, methods and technology disclosed in U.S. Pat. Nos. 8,411,913 and 6,097,035, which are incorporated by reference), as long as the captured image includes part of the fingerprint (e.g. fingerprint that surrounds the drop of blood on the pricked finger) that can be processed to produce information for identification, the image would be acceptable.

In some embodiments, the camera 500 captures one image of the pricked finger 900 and at least two types of information are extracted from the image. The information includes: (1) the fingerprint information that is used to verify the identity of the test subject; and (2) characteristics related to the drop of blood 90. In some embodiments, such characteristics include but are not limited to: size, geometry, shape, position, color, light intensity, light scattering, or other optical indication of the blood sample on the pricked finger 900. In some embodiments, the characteristics of the sample are used to determine whether the blood sample is from the pricked finger 900; in addition, in certain embodiments such characteristics are also used to determine the approximate volume of the sample and whether a correct type of sample (e.g. blood vs. saliva) is collected.

In some embodiments, the camera 500 is also configured to record a video of a part or the entirety of the process of providing the drop of blood for testing. In some embodiments, such a recording ensures that the drop of blood 90 is actually produced by the subject of the test plate 10 through the steps of pricking the finger, squeezing the finger, and depositing the blood by touching the test plate 10, not from other sources such as but not limited to blood prepared beforehand by the subject. In some embodiments, the camera 500 captures the image of the fingerprint of the pricked finger 900 while recording the video of the process of providing the drop of blood for testing. In certain embodiments, recording a video of the process of providing the drop of blood for testing would generate a comprehensive and continuous record of the sample collecting process, allowing the agency/entity/professional that is administering/supervising the testing to be able to monitor, control and authenticate the blood test in full. From the video, it would be clear whether the subject conducted and completed the entire process of producing the drop of blood for testing. In some embodiments, it would be sufficient and/or necessary to record only part of the process of producing the drop of blood for testing. For example, in certain embodiments, only the process of depositing the drop of blood 90 on the test plate 10 is recorded. Such an approach would reduce file size for the recorded data and is still sufficient to determine: (1) whether the drop of blood 90 is actually produced by the pricked finger 900, and (2) whether the drop of blood 90 is deposited on the sample receiving surface 11 of the test plate 10.

In some embodiments, it is impractical, difficult or unnecessary to use the camera 500 to record a video of the process of providing the drop of blood for testing. Therefore, in certain embodiments, the camera 500 is configured to capture one or more images of the drop of blood 90 during the process of providing the blood for testing. For instance, in some embodiments, the camera 500 is configured to capture an image of the drop of blood 90 and the pricked finger 900 before the blood is deposited. Such an image is used to verify that the finger to which the drop of blood 90 is attached to has actually been pricked. In addition, the image is analyzed to determine whether the drop of blood 90 is actually produced from the pricked finger 900, based on the certain characteristics (e.g. geometry, shape, size, position, color, light intensity, and/or light scattering) of the drop of blood 90. In some embodiments, the camera 500 is configured to capture at least two images of the drop of blood 90, one image before the depositing and one image after. In certain embodiments, an analysis of the images and a comparison of them reveals: (1) whether the drop of blood 90 is actually produced from the pricked finger 900, and (2) whether the drop of blood 90 in the first image is actually deposited on the sample receiving surface 11 of the test plate 10.

Authentication by Blood Pattern or Flow

In some embodiments, certain characteristics of sample that are captured by the cameral either still image or video or both will be analyzed to identify if the sample (e.g. blood) is really from the subject's body or was a foreign sample that is put on the subject body. For example, in a finger pricked blood sample, if a blood sample is from the subject body, a video would show the blood drop volume grow with time, and/or a still image will show a blood sample pattern that is consistent with a blood from the subjects' body not from elsewhere. Examples of such characteristics include but are not limited to: size, geometry, shape, position, color, light intensity, light scattering, or other optical indication of the blood sample on the pricked finger 900.

Sample Receiving Area and Camera Positioned on Opposite Side of Test Plate

In some embodiments, the sample receiving area and a camera are position on the opposite side of the test plate (e.g., FIG. 1(B) and FIG. 2(A)), and the camera can see through the plate to observe an object and/event on the other side of the plate, include the sample before and after being deposited on the sample area. Such arrange has many advantage in sample authentication. In some embodiments, the plate is transparent to the camera.

In the two embodiments shown in FIG. 1, panels (A) and (B), the camera 500 is placed at different positions relative to the test plate 10. In general, the plane in which the test plate 10 is positioned divides the relative space into a top space, which faces the sample receiving surface 11, and a bottom space, which faces a non-sample receiving surface of the test plate 10 opposite to the sample receiving surface 11. Panels (A) and (B) of FIG. 1 show two specific positioning designs of the camera 500. In panel (A), the camera 500 is positioned in the top space; the lens 510 of the camera 500 is pointed to the direction of the sample receiving surface 11 and the pricked finger 900, allowing the camera 500 to capture the image(s) and/or video(s) of the process of providing the drop of blood for testing. In some embodiments, the lens 510 is perpendicular to the sample receiving surface 11.

In panel (B) of FIG. 1, and also referring to panel (A) of FIG. 2, the camera 500 is positioned in the bottom space; and the lens 510 of the camera 500 faces a non-sample receiving surface of the test plate. In some embodiments, the test plate 10 is partly or entirely transparent, and the camera 500 is configured to capture the images through the test plate 10.

It should also be noted that the positioning of the camera 500 and the test plate 10, as well as other components of the device of the present invention, vary according to the specific designs of verification process and the specific protocol to capture which type of image(s) and/or video(s). In some embodiments, the camera 500, the test plate 10, as well as other components of the device of the present invention, are integrated together into a single structure.

A Test Device Having Two Plates

In some embodiment, a test plate is used together with a cover plate, namely, a test device comprises a first plate (test plate) and a second plate (cover plate) that are movable to each other. FIG. 4 includes an illustration of an exemplary embodiment of the present invention, showing a test plate that comprises a first plate and second plate that are movable to each other into different configurations. In some embodiments, the test device with two plates are termed QMAX-card or Q-card.

The two plates together can do many functions that a single plate cannot. The function of the two plates include, but not limited to, (a) reshape a sample (e.g. a thin layer), (b) control the sample's thickness, (c) reduce a sample evaporation, (d) protection from damage or contamination, and (e) reduce a change of tempering.

For example, as shown in panel (B) of FIG. 2, the device of the present invention further comprises a cover plate 20, which is used to cover the test plate 10 so that the sample is squeezed into a thin layer for further analysis. In some embodiments, the test plate 10 or the cover plate 20 comprise spacers fixed on the one or both of the test plate 10 and the cover plate 20. In certain embodiments, after the plates are compressed into a face-to-face configuration, the spacers regulate the spacing between the plates. If the sample has been deposited, all or part of the sample is compressed into a thin layer that has a uniform thickness with a small variation. The sample is then analyzed for certain properties, such as but not limited to cell numbers for specific cell types, e.g. red blood cells and white blood cells.

In some embodiment, for the two plate test device, a lock is configured to locked the plate once the sample is deposited. In some embodiment, for the two plate test device, a lock is configured, so that locked the plate once the sample is deposited; and reopening the plates after the locking will be (i) noticed, (ii) damage the sample, or (iii) both.

Spacers

In some embodiments, spacers are placed on the surface of one or both plates of two-plate test device. The spacers regulate the plates spacing and hence the sample thickness when the plates are at a closed configuration. In some embodiments, there is a hinge connected to the two plates. Further descriptions of the two plate device, the spacers, the hinges and the others, which can be integrated with the sample authentication applications, are described in PCT Application (designating U.S.) No. PCT/US2016/045437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016, the complete disclosures of which are hereby incorporated by reference in their entireties for all purposes.

Exhale Breath Condensation Samples

According to the present invention, the breath sample from a subject is also can be authenticated. FIG. 5 includes an illustration of an exemplary embodiment of the present invention, showing identification of breath sample for a subject, where the camera (not shown) can image and video the sample deposition to authenticate a sample from a subject. One example of breath collection device comprises:
a collection plate (i.e. first plate or test plate) and a cover plate (i.e. second plate), wherein:
  i. the plates are movable relative to each other into different configurations;
  ii. one or both plates are flexible;
  iii. each of the plates has, on its respective surface, a sample contact area for contacting a vapor condensate (VC) sample that contains an analyte;
  iv. one or both of the plates comprise spacers that are fixed with a respective plate, wherein the spacers have a predetermined substantially uniform height and a predetermined constant inter-spacer distance and wherein at least one of the spacers is inside the sample contact area;
wherein one of the configurations is an open configuration, in which: the two plates are either completely or partially separated apart, the spacing between the plates is not regulated by the spacers, and the VC sample is deposited on one or both of the plates; and
wherein another of the configurations is a closed configuration which is configured after the VC sample deposition in the open configuration; and in the closed configuration: at least a part of the VC sample is between the two plates and in contact with the two plates, and has a highly uniform thickness that is regulated by the spacers and the two sample surfaces of the plates and is equal to or less than 30 um with a small variation.

In some embodiments, the device further comprises, on one or both plates, one or a plurality of dry binding sites and/or one or a plurality of reagent sites. In some embodiments, the sample is exhale breath condensate.

In some embodiments, the sample is a vapor from a biological sample, an environmental sample, a chemical sample, or clinical sample. In some embodiments, wherein the analyte comprises a molecule (e.g., a protein, peptides, DNA, RNA, nucleic acid, or other molecules), cells, tissues, viruses, and nanoparticles with different shapes. In some embodiments, wherein the analyte comprises volatile organic compounds (VOCs). In some embodiments, wherein the analyte comprises nitrogen, oxygen, $CO_2$, $H_2O$, and inert gases. In some embodiments, wherein the analyte is stained.

The same approaches for blood sample authentication described in the disclosure can be used for the breath authentification. The biometric identifier related to the breath of a subject includes but is not limited to: facial identifications, lips, eyes, nose, ear, etc.

Further description of breath collection and detections is give in PCT Application, PCT/US16?51794 filed on Sep. 14, 2016, which are incorporated herein in its entirety for all purposes.

Adaptor (Housing)

In some embodiments, the camera 500 and the test plate 10 are physically integrated together, e.g. in a single housing structure, which is termed as "adaptor".

A system for authenticating a sample from a subject being tested comprising: (a) a device of any of prior claims; and (b) an adaptor that is configured to connect to a camera and comprises a slot, wherein i. the slot is dimensioned to receive and position the device; and ii. the adaptor is configured to fix, after the device in the slot, the relative position between the device and the camera.

In certain embodiments, the camera 500 and the test plate 10 are partially or entirely separated apart but are considered parts of one device.

Sample Testing Together with Sample Collection

In some embodiments, after the drop of a sample (e.g. blood 90) is deposited on the test plate 10, further processing, testing and/or analysis of the sample is conducted. In some embodiments, the same camera that is used for sample authentication is used for the sample analysis.

In some embodiments, the analysis is immediate after the sample deposition.

In some embodiments, for the two plate test device, the analysis is immediate after pressing the two plates into a closed configuration.

In some embodiments, the analysis is done by a smartphone. In some embodiments, the analysis use a light source.

Authentication and Analysis without Sample Transportation

In some embodiments, a sample from a subject is collected by a test device, authenticated, and measured without a transportation of the test device away from the sample collection location, which is termed as "one-short analysis". In some embodiments, the one-short analysis is performed by the same camera of the authentication and analysis. In some embodiments, the one-short analysis is performed by two or more camera of the authentication and analysis.

Identification Labels, Timer, and Others

In certain embodiments, the test plate is further configured to prevent sample switching after the deposition. As shown in FIG. 1, panels (A) and (B), and FIG. 2, panel (A), the test plate 10 comprises a plate identification (ID) 16. The plate ID 16 is any combination of numerical, graphical, alphabetical, symbolic, or other characters and signs, as long as the plate ID 16 can be used to identify the test plate 10 uniquely. For example, in certain embodiments the plate ID 16 is a sequence of digital and/or alphabetical characters, a barcode, a QR code, or other machine-readable non-letter type code. In some embodiments, the plate ID 16 is positioned on the sample receiving surface 11 of the test plate 10, as shown in FIG. 1. In certain embodiments, the plate ID 16 is also positioned on other parts of the plate, e.g. on the non-sample receiving surface of the test plate 10. In some embodiments, the camera 500 is configured to capture an image of the plate ID 16 during the process of providing a drop of blood for testing. For example, when taking the image of the fingerprint of the pricked finger 900 and/or recording a video of the process of providing a drop of blood for testing, the camera 500 captures one or images of the test plate 10 and such images show the plate ID 16.

The plate ID 16 is used to identify the test plate 10, as well as the blood sample deposited on the test plate 10. The plate ID 16 is also combined with the fingerprint information extracted from the image of the pricked finger 900. For example, it would be possible to match the fingerprint from the pricked finger 900 to stored fingerprint information of the intended subject, and at the same time use the plate ID and the video(s)/image(s) captured during the process of providing the drop of blood for testing to clearly identify the test plate 10 and ensure that the fingerprint image matches the video(s)/image(s) on record. In some embodiments, the presence of the plate ID 16 allows the agency/entity/professional administering the test to prevent switching the plate after the sample has been deposited. In certain embodiments, to prevent switching, a compressed regulated open flow (CROF) test plate is used.

In some embodiments, the camera 500 includes a timing component, which records the particular time points during the process of providing the drop of blood for testing. For example, the time point of pricking the finger is recorded as US Eastern Time 2016-10-01 9:30:25 AM; the time point of depositing the drop of blood 90 is recorded as US ET 2016-10-01 9:30:50 AM. The recording of the time point(s) is conducted by the timing component of the camera 500, or is conducted by a timing component physically separated from the camera 500 but still be considered part of a single device. The recorded time points are used to add another layer of authentication for the blood test. For example, the recorded time is compared with other records to verify whether the process of providing the drop of blood for testing is conducted at the prescribed time by the agency/entity/professional administering the test. In addition, the time period between the recorded time points provides further information/suspicion about the authenticity of the blood test. For instance, if there is a three-minute gap between the time point of squeezing the pricked finger and the time point of depositing the drop of blood, then it becomes suspicious as to whether the drop of blood produced by the pricking and squeezing is actually the drop of blood deposited on the test plate 10. A follow-up investigation (e.g. human reviewing of the image(s) and/or video(s)) becomes necessary and can reveal further evidence of wrongdoing.

In some embodiments, the device of the present invention further comprises a processor, which is configured to process the images and/or video captured by the camera 500. In certain embodiments, the processor is a component of the camera 500 or be integrated with the camera 500 physically into a single structure. For example, the processor and the camera 500 are both parts of a computing device, such as but not limited to a mobile phone, a tablet computer or a laptop computer. Alternatively, the processor, the camera 500, the timing component are all parts of a computing device. In addition, the processor, the camera 500, the timing component, and the test plate 10 are all parts of a device, wherein in some embodiments the parts are integrated together and in some embodiments the parts are separated apart.

In some embodiments, the processor is configured to process and analyze the images and videos captured by the camera 500. For example, in certain embodiments, the processor is configured to: analyze the image of the fingerprint captured by the camera 500, compare the fingerprint with stored fingerprint information of the subject; and/or determine whether the blood provided in the blood test is authentic. In some embodiments, the processor is configured to: analyze the image of the drop of blood before depositing, and determine whether the drop of blood is truly produced by pricking and squeezing the subject's finger.

More Examples of Biometric Identifier

As indicated, besides fingerprints, in some embodiments of the present invention, other biometric identifiers are used for identification of the subject being tested. For example, in certain embodiments the biometric identifier is palmprints. The image(s)/video(s) captured by the camera 500 include palmprints of the hand and the palmprints are compared to the palmprint information on file for the intended subject. In some embodiments, the technologies to verify palmprint information are known. Such technologies include but not are limited to the devices, apparatus, and methods disclosed in U.S. Pat. Pub. Nos. 2012/0194662 and 2005/0281438, and U.S. Pat. Nos. 8,229,178, 7,466,846, 8,135,181, 8,265,347, and 7,496,214, which are all incorporated by reference in their entireties.

In certain embodiments of the present invention, the biometric identifier is hand geometry, which is s a biometric that identifies users by the shape of their hands. In known technologies, hand geometry readers measure a user's hand along many dimensions and compare those measurements to measurements stored in a file. In some embodiments, the image(s)/video(s) captured by the camera 500 provides hand geometry of the hand and the hand geometry is compared to information on file for the intended subject. In some embodiments, the technologies to verify hand geometry information are known. Such technologies include but not are limited to the devices, apparatus, and methods disclosed in U.S. Pat. Pub. Nos. 2016/0253658 and 2011/0175986, and U.S. Pat. Nos. 7,886,157, 9,336,634, 8,358,336, 8,279,042, 7,660,442, 7,616,784, 4,720,869, and 6,628,810, which are all incorporated by reference in their entireties.

In certain embodiments of the present invention, the biometric identifier is vein pattern of the hand, wherein vein patterns (or vascular patterns) are used for biometric identification through the analysis of the patterns of blood vessels visible from the surface of the skin. The image(s)/video(s) captured by the camera 500 provide vein pattern of the hand and the vein pattern are compared to information on file for the intended subject. In some embodiments, the technologies to verify vein pattern information are known. Such technologies include but not are limited to the devices, apparatus, and methods disclosed in U.S. Pat. Pub. Nos. 2014/0196131, 2010/0119122 and 2010/0226545, and U.S. Pat. Nos. 8,803,963, 9,095,285, 9,289,160, 8,509,495, 8,275,174 and 9,317,761, which are all incorporated by reference in their entireties.

In certain embodiments of the present invention, the biometric identifier is sweat pores of the hand, wherein positions and patterns of the sweat pores are used for biometric identification of the subject. The image(s)/video(s) captured by the camera 500 include sweat pores of the hand and the sweat pores are compared to information on file for the intended subject. In some embodiments, the technologies to verify sweat pores information are known. Such technologies include but are not limited to the devices, apparatus, and methods disclosed in U.S. Pat. Pub. Nos. 2007/0003114 and 2014/0294262, and U.S. Pat. Nos. 6,228,029, 8,663,108, and 8,744,139, which are all incorporated by reference in their entireties.

In certain embodiments of the present invention, the biometric identifier is fingernail beds of the hand, wherein shapes, sizes and colors of the fingernail beds are used for biometric identification of the subject. The image(s)/video(s) captured by the camera 500 include fingernail beds of the hand and the fingernail beds are compared to information on file for the intended subject. In some embodiments, the technologies to verify fingernail beds information are known. Such technologies include but are not limited to the devices, apparatus, and methods disclosed in U.S. Pat. Pub. No. 2007/0003114 and U.S. Pat. Nos. 6,631,199 and 5,751,835, which are all incorporated by reference in their entireties.

In some embodiments, the identity of the subject being tested is verified by one biometric identifier. In certain embodiments, the identity of the subject being tested is verified by at least two biometric identifiers; in certain embodiments, the identity of the subject being tested is verified by at least three biometric identifiers; in certain embodiments, the identity of the subject being tested is verified by four or more biometric identifiers.

Packed Testing Plates

FIG. 3 shows a perspective view of a package 600 and the test plate 10. In some embodiments, the test plate 10 is sealed in a package 600 before the blood test. For clarity purposes, FIG. 3 shows the package 600 and the test plate 10 when the test plate 10 is exposed. In certain embodiments, the package 600 is sealed before the blood test and the test plate 10 is not accessed and/or seen without opening the package 600. In some embodiments, the package 600 is opaque. It should also be noted that in some embodiments package 600 also contains other components of the present invention, such as but not limited to the cover plate 20, the camera 500, the processor, and the timing component. As indicated above, in some embodiments, some or all of the components are integrated together. In some embodiments, the integrated components would be contained in a single package.

As shown in FIG. 3, the package comprises a package identification (ID) 601, which is any combination of numerical, alphabetical, symbolic or other characters and signs, as long as the package ID 601 can be used to identity the package 600 uniquely. In some embodiments, the device of the present invention uses the package ID 601 to identify the package 600.

In some embodiments, the package ID 601 is paired with the plate ID 16 and the pairing is unknown to the subject. During the design/manufacturing of the device related to the blood test, a design/manufacturing system generate pairs of the package ID 601 and the plate ID 16; such pairing is store by the system and it is not accessible or known by the subject. The agency/entity/professional administering the blood test does or does not know the pairing. In other words, the subject only sees the test plate 10 (and the plate ID 16) for the first time after opening the package 600. It would impossible for the subject to prepare a fake plate beforehand because he/she does not know the plate ID 16.

Other Embodiment Examples of Present Invention

In some embodiments, the test plate 10 is part of a compressed regulated open flow (CROF) device (also termed as QMAX device; Q: quantification; M: magnifying; A: adding reagents; X: acceleration), such as but not limited to the CROF device described PCT Application (designating U.S.) No. PCT/US2016/045437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016, the complete disclosures of which are hereby incorporated by reference in their entireties for all purposes.

In some embodiments, the test plate 10 is part of a QMAX (Q: quantification; M: magnifying; A: adding reagents; X: acceleration) card, which is a QMAX device with a connecting structure such as but not limited to a hinge. In certain embodiments, the test plate 10 and cover plate 20 are parts of the QMAX card. In part, the QMAX card is described in the patents/applications referenced above, as well as in U.S. Provisional Patent Application No. 62/431,639, which was filed on Aug. 10, 2015, which was filed on Dec. 9, 2016, the complete disclosures of which are hereby incorporated by reference in their entireties for all purposes.

Analyte, Sample and Application

In some embodiments, the analyte in the sample to be detected in the assay comprises, but not limited to, cells, viruses, proteins, peptides, DNAs, RNAs, oligonucleotides, and any combination thereof.

In some embodiments, the present invention finds use in detecting biomarkers for a disease or disease state. In certain instances, the present invention finds use in detecting biomarkers for the characterization of cell signaling pathways and intracellular communication for drug discovery and vaccine development. For example, the present invention can be used to detect and/or quantify the amount of biomarkers in diseased, healthy or benign samples. In certain embodiments, the present invention finds use in detecting biomarkers for an infectious disease or disease state. In some cases, the biomarkers can be molecular biomarkers, such as but not limited to proteins, nucleic acids, carbohydrates, small molecules, and the like. The present invention find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

The device and method of the present invention are used in health monitoring, mobile monitoring, or crime monitoring. In addition, the device and method the present invention can be used for insurance, for health improvement, or for medication purposes.

Cloud

The devices/apparatus, systems, and methods herein disclosed can employ cloud technology for data transfer, storage, and/or analysis. The related cloud technologies are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, all of which applications are incorporated herein in their entireties for all purposes.

In some embodiments, the cloud storage and computing technologies can involve a cloud database. Merely by way of example, the cloud platform can include a private cloud, a public cloud, a hybrid cloud, a community cloud, a distributed cloud, an inter-cloud, a multi-cloud, or the like, or any combination thereof. In some embodiments, the mobile device (e.g. smartphone) can be connected to the cloud through any type of network, including a local area network (LAN) or a wide area network (WAN).

In some embodiments, the data (e.g. images of the sample) related to the sample is sent to the cloud without processing by the mobile device and further analysis can be conducted remotely. In some embodiments, the data related to the sample is processed by the mobile device and the results are sent to the cloud. In some embodiments, both the raw data and the results are transmitted to the cloud.

Second Group of Other Examples of Present Invention

Further examples of inventive subject matter according to the present disclosure are described in the following enumerated paragraphs.

A1. A device for authenticating a blood sample from a subject being tested, comprising:
 (a) the test plate comprises a plate having a sample contact area on its surface that receives a blood sample from a pricked body part of a subject that is being tested; and
 (b) a camera that is configured, during a sample deposition in which the blood sample on the pricked body part is directly deposited onto the sample contacting area of the test plate, the camera is configured to capture:
  i. one or more images of the blood sample on the pricked body part together with at least one biometric identifier associated with the subject, and/or
  ii. a video of a part or an entirety of the blood sample deposition.

A2. A device for authenticating a sample of a subject being tested, comprising:
 (a) a test plate that comprises a first plate and a second plate, wherein:
  i. the first plate and second plate are movable relative to each other into different configurations, including an open configuration and a closed configuration;
  ii. the first plate comprises a surface that has a sample contact area for receiving a sample of a subject that is being tested; and
 (b) a camera that is configured, during a sample deposition in which the sample on a subject body is directly deposited onto the sample contacting area of the first plate, to capture:
  i. one or more images of the sample together with at least one biometric identifier associated with the subject, and
  ii. a video of a part or an entirety of the blood sample deposition,
  wherein an open configuration is the configuration, in which the two plates are partially or entirely separated apart, and the blood sample is deposited on the sample contact area; and
  wherein a closed configuration is the configuration, in which, the inner surfaces of the two plates are in contact the sample.

A3. The device of any prior embodiments, wherein the plate that receives that sample is transparent, the sample receiving area is one side of the plate, and the camera is on the other side of the plate, wherein the camera is capable of imaging, through the plate, an object on the sample receiving area side of the plate.

A4. The device of any prior embodiments, wherein the device further comprise (i) microprocessor and (ii) an algorithm, wherein the microprocessor and the algorithm are configured to analyze the video and/or the image to determine if the sample is deposited on the test plate is from the subject that is intended to be tested.

A5. A system for authenticating a sample from a subject being tested comprising:
(a) a device of any of prior claims; and
(b) an adaptor that is configured to connect to a camera and comprises a slot, wherein
  i. the slot is dimensioned to receive and position the device; and
  ii. the adaptor is configured to fix, after the device in the slot, the relative position between the device and the camera.

A6. A method of authenticating a blood test from a subject that to be tested, comprising:
(a) providing a device of any of prior claims;
(b) providing a camera;
(c) pricking a body part of a subject being tested and allowing a blood sample to emerge on the pricked body part;
(d) depositing the blood sample onto the sample receiving area by making the blood sample directly contact the sample receiving area; and
(e) during the deposition process (d), using the camera to capture:
  i. one or more image of the blood sample together with at least one biometric identifier of the hand of the subject being tested, and/or
  ii. a video of a part or an entirety of the deposition process.

A7. A method of authenticating a sample from a subject that to be tested, comprising:
(a) providing a device of any of prior claims;
(b) providing a camera;
(c) deposit a sample from a subject that to be tested from the subject to the device; and
(d) during the deposition process (c), using the camera to capture:
  iii. one or more image of the blood sample together with at least one biometric identifier of the hand of the subject being tested, and/or
  iv. a video of a part or an entirety of the deposition process.

A8. The device, method, or system of any prior embodiments, wherein the camera is configured to measure an analyte in the blood or the exhale breath condensation.

A9. The device, method, or system of any prior embodiments, wherein the device further comprises a hinge, and the first plate and second plate are connected by the hinge and movable relative to each other around the axis of the hinge into different configurations.

A10. The device, method, or system of any prior embodiments, wherein the device further comprises spacers, wherein at a closed configuration, the spaces regulates a spacing between the first and the second plate.

A11. The device, method, or system of any prior embodiments, wherein the sample is a breath sample.

A12. The device, method, or system of any prior embodiments, wherein the sample is a blood sample.

A13. The device, method, or system of any prior embodiments, wherein the sample is a saliva sample.

A14. The device, method, or system of any prior embodiments, wherein the camera is a part of mobile phone.

A15. The device, method, or system of any prior embodiments, wherein the camera is a part of mobile phone, wherein the mobile phone has a second camera for testing the test plate.

A16. The device, method, or system of any prior embodiments, wherein the biometric identifier is fingerprint of the pricked finger.

A17. The device, method, or system of any prior embodiments, wherein the biometric identifier is fingerprint of a finger that is not pricked.

A18. The device, method, or system of any prior embodiments, wherein the biometric identifier is palmprint of the hand.

A19. The device, method, or system of any prior embodiments, wherein the biometric identifier is hand geometry of the hand.

A20. The device, method, or system of any prior embodiments, wherein the biometric identifier is vein pattern of the hand.

A21. The device, method, or system of any prior embodiments, wherein the biometric identifier is sweat pores of the hand.

A22. The device, method, or system of any prior embodiments, wherein the biometric identifier is fingernail beds of the hand.

A23. The device, method, or system of any prior embodiments, wherein the one or more images include at least two biometric identifiers, and each biometric identifier is selected from the group consisting of: fingerprint of the pricked finger, fingerprint of a finger that is not pricked, palmprint of the hand, hand geometry of the hand, vein pattern of the hand, sweat pores of the hand, and fingernail beds of the hand, wherein the at least two biometric identifiers are used to determine that the subject being tested is an intended subject.

A24. The device, method, or system of any prior embodiments, wherein the one or more images include at least three biometric identifiers, and each biometric identifier is selected from the group consisting of: fingerprint of the pricked finger, fingerprint of a finger that is not pricked, palmprint of the hand, hand geometry of the hand, vein pattern of the hand, sweat pores of the hand, and fingernail beds of the hand, wherein the at least three biometric identifiers are used to determine that the subject being tested is an intended subject.

A25. The device, method, or system of any prior embodiments, wherein at least one image in step (i) is recorded before the blood sample touches the sample receiving area.

A26. The device, method, or system of any prior embodiments, wherein at least image in step (i) is recorded after the blood sample touches the sample receiving area.

A27 The device, method, or system of any prior embodiments, wherein the images in step (i) are recorded both before and after the blood sample touches the sample receiving area.

A28. The device of any prior paragraphs, wherein further comprising hardware and software which are configured to process and analyze the images/videos.

A29. The device of any prior paragraphs, wherein the hardware is a mobile phone and has local and long distance communication capacities.

A30. The device of any prior paragraphs, wherein the hardware and software are configured to analyze an image of the blood on the pricked finger before the direct blood sample deposition to evaluate the likelihood that the blood sample on the pricked finger recorded in the image is from the pricked finger.

A31. The device of any prior paragraphs, wherein the evaluation of likelihood comprises an evaluation of the size, shape, geometry, color, light intensity and/or light scattering of the blood sample on the pricked finger.

A32. The device, method, or system of any prior embodiments, wherein the positions of the test plate and the camera are configured to have the camera imaging both the pricked finger and the test plate in the same image frame.

A33. The device of any prior paragraphs, wherein further comprising an optical fiber that is configured to image the pricked finger or the test plate by camera.

A34. The device, method, or system of any prior embodiments, wherein the test plate comprises a plate identification.

A35. The device, method, or system of any prior embodiments, wherein the camera is configured to capture an image or video that includes the plate identification.

A36. The device, method, or system of any prior embodiments, wherein the camera is configured to capture images or videos of the blood sample, the biometric identifier, the test plates, and the plate identification.

A37. The device, method, or system of any prior embodiments, wherein:
  i. the test plate is sealed in a package before the blood test; and
  ii. the package comprises a package ID.

A38. The device of embodiments A34 to A35, wherein the package ID is paired with the plate ID and the pairing is unknown to the subject being tested.

A39. The device, method, or system of any prior embodiments, wherein the method analyzing a sample comprises evaluation of the video (time evolution of image) of the shape of the blood sample on the pricked body part.

A40. The device, method, or system of any prior embodiments, wherein the method further comprising: using the camera to capture a time point for depositing the blood sample on the test plate.

A41. The device, method, or system of any prior embodiments, wherein the device is used for health monitoring, mobile monitoring, crime monitoring, for insurance, for health, and/or for medication.

A42. The device, method, or system of any prior embodiments, wherein the test plate is further configured to prevent sample switching after the deposition.

A43. The device of paragraph 29, wherein the prevention of sample switching comprises using of a CROF (Compressed Open Flow) test plate.

A44. The device, method, or system of any prior embodiments, wherein the biometric identifier is selected from the group consisting of: fingerprint of the pricked finger, fingerprint of a finger that is not pricked, palmprint of the hand, hand geometry of the hand, vein pattern of the hand, sweat pores of the hand, and fingernail beds of the hand.

A45. The device, method, or system of any prior embodiments, wherein the method further comprising:
  (a) analyzing the one or more images that include the biometric identifier;
  (b) comparing the biometric identifier to stored biometric information from the intended subject; and
  (c) determining whether the sample provided in the sample test is authentic.

A46. The device, method, or system of any prior embodiments, wherein the method further comprising:
  (a) using the camera to capture an image of the drop of blood on a subject's body surface before depositing the sample on test plate;
  (b) analyzing the image of the drop of blood; and
  (c) determining whether the drop of blood is truly produced from a subject's body.

A47. The device, method, or system of any prior embodiments, wherein the method analyzing the image comprises evaluation of the geometry and/or shape of the blood sample of a pricked body part.

A48. The device, method, or system of any prior embodiments, wherein the method collect a sample from a subject using by a test device, authenticate the sample, and analyze the sample without transporting the test device away from the sample collection location.

A49. The device, method, or system of any prior embodiments, wherein the method collect a sample from a subject using by a test device, authenticate the sample, and analyze the sample without transporting the test device away from the sample collection location, wherein the authentication and analysis using the same camera.

A50. The device, method, or system of any prior embodiments, wherein the method collect a sample from a subject using by a test device, authenticate the sample, and analyze the sample without transporting the test device away from the sample collection location, wherein the authentication and analysis wherein the authentication and analysis use two or more cameras.

Additional Notes

Further examples of inventive subject matter according to the present disclosure are described in the following enumerated embodiments.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

The invention claimed is:

1. A device for authenticating a blood sample from a subject being tested, comprising:
   (a) a test plate comprising a first plate, a second plate, and spacers, wherein:
      i. the first plate and second plate are movable relative to each other into different configurations, including an open configuration and a closed configuration;
      ii. the first plate and the second plate comprise a sample contact area on its surface that receives a blood sample from a pricked body part of a subject that is being tested; and
      iii. the spacers are placed on one or both of the first plate and the second plate,
      wherein the open configuration is the configuration in which the two plates are partially or entirely separated apart, and the blood sample is deposited on one or both of the plates,
      wherein the closed configuration is the configuration in which (i) the sample contact areas of the two plates are in contact with the blood sample, and (ii) the spacers regulate a spacing between the first plate and the second plate; and
   (b) a camera that is configured, during a sample deposition in which the blood sample from the pricked body part is directly deposited onto the sample contact area of the test plate, to capture at least one of:
      i. one or more images of the blood sample from the pricked body part together with at least one biometric identifier associated with the subject, and
      ii. a video of a part or an entirety of the blood sample deposition.

2. A device for authenticating a sample of a subject being tested, comprising:
   (a) a test plate that comprises a first plate and a second plate, wherein:
      i. the first plate and second plate are movable relative to each other into different configurations, including an open configuration and a closed configuration; and
      ii. the first plate comprises a surface that has a sample contact area for receiving a sample of a subject that is being tested; and
   (b) a camera that is configured, during a sample deposition in which the sample of the subject is directly deposited onto the sample contact area of the first plate, to capture at least one of:
      i. one or more images of the sample together with at least one biometric identifier associated with the subject, and
      ii. a video of a part or an entirety of the sample deposition,
   wherein the open configuration is the configuration in which the two plates are partially or entirely separated apart, and the blood sample is deposited on the sample contact area; and
   wherein the closed configuration is the configuration in which the sample contact areas of the two plates are in contact with the sample.

3. The device of claim 2, wherein the plate that receives the sample is transparent, wherein the sample contact area is one side of the plate, wherein the camera is on the other side of the plate, and wherein the camera is capable of imaging, through the plate, an object on the sample contact area side of the plate.

4. The device of claim 2, wherein the device further comprises (i) a microprocessor and (ii) an algorithm, wherein the microprocessor and the algorithm are configured to analyze the video and/or the one or more images to determine if the sample deposited on the test plate is from the subject that is intended to be tested.

5. A system for authenticating a sample from a subject being tested comprising:
   (a) the device of claim 2; and
   (b) an adaptor that is configured to connect to the camera and comprises a slot, wherein
      i. the slot is dimensioned to receive and position the device; and
      ii. the adaptor is configured to fix, after the device is in the slot, the relative position between the device and the camera.

6. A method of authenticating a blood test from a subject that to be tested, comprising:
   (a) providing the device of claim 2;
   (b) pricking the body part of the subject being tested and allowing the sample to emerge on the pricked body part;
   (c) depositing the blood sample onto the sample contact area by making the blood sample directly contact the sample contact area; and
   (d) during the deposition process (c), using the camera to capture:
      i. one or more images of the blood sample together with at least one biometric identifier of the hand of the subject being tested; and/or
      ii. a video of a part or an entirety of the deposition process.

7. A method of authenticating a sample from a subject that to be tested, comprising:
   (a) providing the device of claim 2;
   (b) depositing the sample from the subject to be tested onto the device; and (c) during the deposition process (b), using the camera to capture:
   i. one or more images of the sample together with at least one biometric identifier of the subject being tested; and/or
   ii. a video of a part or an entirety of the deposition process.

8. The method of claim 7, wherein analyzing the sample comprises evaluation of the video (time evolution of image) of the shape of the blood sample from the pricked body part.

9. The method of claim 7, wherein the method further comprises using the camera to capture a time point for depositing the blood sample on the test plate.

10. The method of claim 7, wherein the device is used for health monitoring, mobile monitoring, crime monitoring, insurance, health, and/or medication.

11. The method of claim 7, wherein the method further comprises:
   (a) analyzing the one or more images that include the biometric identifier;
   (b) comparing the biometric identifier to stored biometric information from the intended subject; and
   (c) determining whether the sample provided in the test plate is authentic.

12. The method of claim 7, wherein the method further comprises:
   (a) using the camera to capture an image of the drop of blood on a subject's body surface before depositing the sample on test plate;
   (b) analyzing the image of the drop of blood; and
   (c) determining whether the drop of blood is truly produced from a subject's body.

13. The method of claim 7, wherein analyzing the image comprises evaluation of a geometry and/or a shape of the blood sample from a pricked body part.

14. The method of claim 7, wherein the method further comprises collecting a sample from a subject using a test device, authenticating the sample, and analyzing the sample without transporting the test device to away from the sample collection location.

15. The method of claim 7, wherein the method further comprises collecting a sample from a subject using a test device, authenticating the sample, and analyzing the sample without transporting the test device to away from the sample collection location, wherein the authentication and the analysis use the same camera.

16. The method of claim 7, wherein the method further comprises collecting a sample from a subject using a test device, authenticating the sample, and analyzing the sample without transporting the test device to away from the sample collection location, wherein the authentication and the analysis use two or more cameras.

17. The device of claim 2, wherein the camera is configured to measure an analyte in the sample, and wherein the sample comprises blood or exhale breath condensation.

18. The device of claim 2, wherein the device further comprises a hinge, and the first plate and second plate are connected by the hinge and movable relative to each other around an axis of the hinge into different configurations.

19. The device of claim 2, wherein the device further comprises spacers, wherein at the closed configuration, the spacers regulate a spacing between the first and the second plate, and the inner surfaces of the two plates are in contact with the sample and compress the blood sample into a layer of uniform thickness.

20. The device of claim 2, wherein the sample is a breath sample.

21. The device of claim 2, wherein the sample is a blood sample.

22. The device of claim 2, wherein the sample is a saliva sample.

23. The device of claim 2, wherein the camera is a part of mobile phone.

24. The device of claim 2, wherein the camera is a part of mobile phone, wherein the mobile phone has a second camera for testing the test plate.

25. The device of claim 2, wherein the biometric identifier is a fingerprint of the pricked finger.

26. The device of claim 2, wherein the biometric identifier is a fingerprint of a finger that is not pricked.

27. The device of claim 2, wherein the biometric identifier is a palmprint of the hand.

28. The device of claim 2, wherein the biometric identifier is a hand geometry of the hand.

29. The method of claim 2, wherein the biometric identifier is a vein pattern of the hand.

30. The device of claim 2, wherein the biometric identifier is sweat pores of the hand.

31. The device of claim 2, wherein the biometric identifier is fingernail beds of the hand.

32. The device of claim 2, wherein the one or more images include at least two biometric identifiers, and each biometric identifier is selected from the group consisting of: a fingerprint of the pricked finger, a fingerprint of a finger that is not pricked, a palmprint of the hand, a hand geometry of the hand, a vein pattern of the hand, sweat pores of the hand, and fingernail beds of the hand, wherein the at least two biometric identifiers are used to determine that the subject being tested is an intended subject.

33. The device of claim 2, wherein the one or more images include at least three biometric identifiers, and each biometric identifier is selected from the group consisting of: a fingerprint of the pricked finger, a fingerprint of a finger that is not pricked, a palmprint of the hand, a hand geometry of the hand, a vein pattern of the hand, sweat pores of the hand, and fingernail beds of the hand, wherein the at least three biometric identifiers are used to determine that the subject being tested is an intended subject.

34. The device of claim 2, wherein the one or more images in step (b)(i) is recorded before the blood sample touches the sample contact area.

35. The device of claim 2, wherein the one or more images in step (b)(i) is recorded after the blood sample touches the sample contact area.

36. The device of claim 2, wherein the one or more images in step (b)(i) are recorded both before and after the blood sample touches the sample receiving area.

37. The device of claim 2, further comprising hardware and software which are configured to process and analyze the one or more images and/or the video.

38. The device of claim 2, wherein the hardware is a mobile phone and has local and long distance communication capacities.

39. The device of claim 2, wherein the hardware and the software are configured to analyze an image of the blood on the pricked finger before the blood sample deposition to evaluate a likelihood that the blood sample from the pricked finger recorded in the image is from the pricked finger.

40. The device of claim 2, wherein the evaluation of the likelihood comprises an evaluation of the size, shape, geometry, color, light intensity and/or light scattering of the blood sample from the pricked finger.

41. The device of claim 2, wherein the position of the test plate and the camera are configured to have the camera imaging both the pricked finger and the test plate in the same image frame.

42. The device of claim 2, further comprising an optical fiber that is configured to image the pricked finger or the test plate by the camera.

43. The device of claim 2, wherein the test plate comprises a plate identification.

44. The device of claim 2, wherein the camera is configured to capture the one or more images or the video that includes the plate identification.

45. The device of claim 2, wherein the camera is configured to capture the one or more images or the videos of the blood sample, the biometric identifier, the test plates, and the plate identification.

46. The device of claim 2, wherein:
   i. the test plate is sealed in a package before the blood test; and
   ii. the package comprises a package ID.

47. The device of claim 46, wherein the package ID is paired with the plate ID and the pairing is unknown to the subject being tested.

48. The device of claim 2, wherein the test plate is further configured to prevent sample switching after the deposition.

49. The device of claim 48, wherein the prevention of sample switching comprises using of a CROF (Compressed Open Flow) test plate.

50. The device of claim 2, wherein the biometric identifier is at least one selected from the group consisting of: fingerprint of the pricked finger, fingerprint of a finger that is not pricked, palmprint of the hand, hand geometry of the hand, vein pattern of the hand, sweat pores of the hand, and fingernail beds of the hand.

* * * * *